United States Patent [19]
Boretos et al.

[11] 4,056,854
[45] Nov. 8, 1977

[54] AORTIC HEART VALVE CATHETER

[75] Inventors: John W. Boretos, Rockville, Md.; Robert A. Poirier, Rochester, Minn.

[73] Assignee: The United States of America as represented by the Department of Health, Education and Welfare, Washington, D.C.

[21] Appl. No.: 727,528

[22] Filed: Sept. 28, 1976

[51] Int. Cl.² .............................................. A61F 1/22
[52] U.S. Cl. ........................................ 3/1.5; 128/1 R; 128/348
[58] Field of Search .................... 3/1.5; 128/1 R, 1 D, 128/303 R, 345, 348, 350 R, 334 R, 334 C

[56] References Cited
U.S. PATENT DOCUMENTS

| | | | |
|---|---|---|---|
| 3,548,417 | 12/1970 | Kischer et al. | 3/1.5 |
| 3,592,183 | 7/1971 | Watkins et al. | 128/1 D |
| 3,671,979 | 6/1972 | Moulopoulos | 3/1.5 |
| 3,874,388 | 4/1975 | King et al. | 128/334 C X |
| 3,952,747 | 4/1976 | Kimmell | 128/348 X |

*Primary Examiner*—Dalton L. Truluck
*Attorney, Agent, or Firm*—John S. Roberts, Jr.; Norman J. Latker; Thomas G. Ferris

[57] ABSTRACT

An artificial valve remotely placeable in a blood vessel without major surgery to supplant the function of a malfunctioning natural valve including an expansible check valve remotely placed in a constricted configuration through the vessel and a remotely removable constraint for selective expansion of the check valve for sealing engagement thereof within the walls of the vessel at the desired location.

8 Claims, 7 Drawing Figures

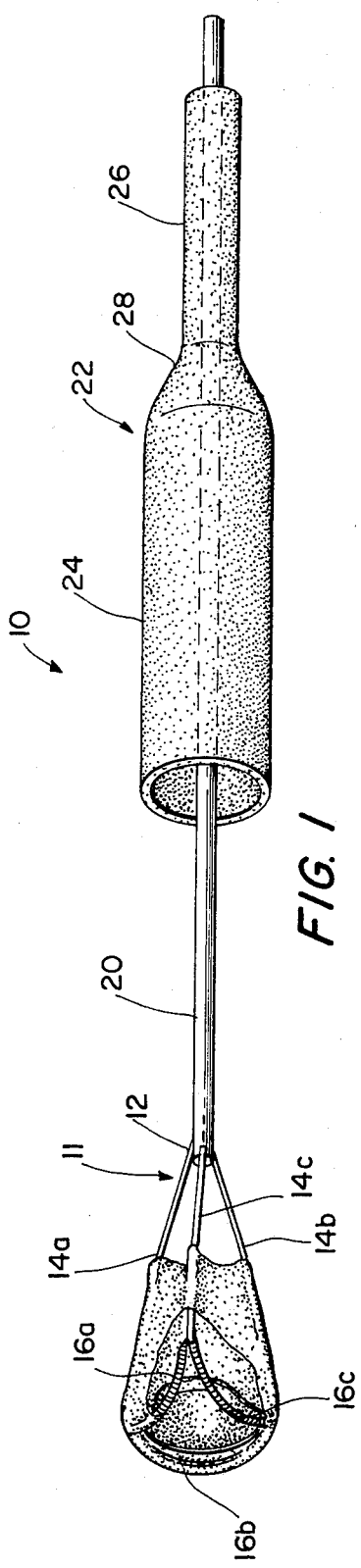
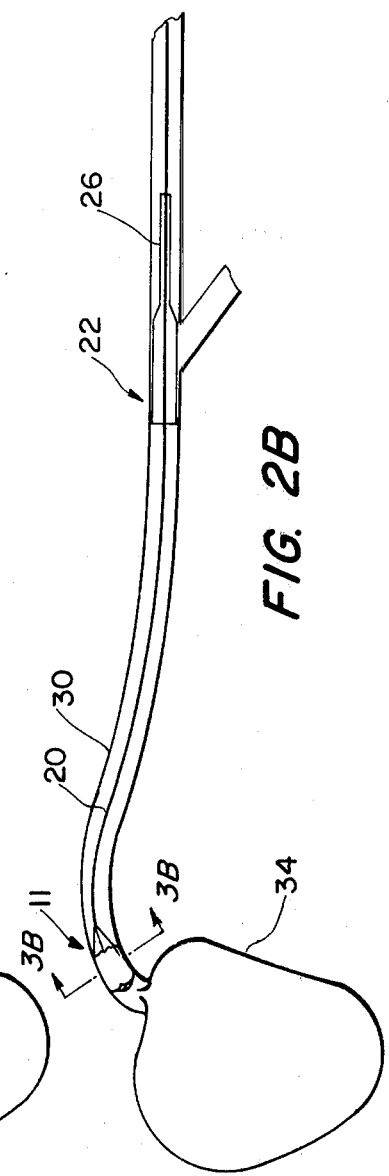

AORTIC HEART VALVE CATHETER

BACKGROUND OF THE INVENTION

With certain malfunctions of natural valves in the body, it is desirable to replace that valve.

It is known in the art that natural heart valves can be replaced with prosthetic valves. Such replacement has heretofore generally been accomplished through major, open chest surgery. Such serious surgery results in a high mortality rate when the patient is in overt heart failure or pulmonary edema.

Recent developments have provided catheter-mounted valves which can be inserted in a major vessel at a point remote from the heart and positioned, through the vessel, proximate to a malfunctioning aortic valve thereby avoiding major surgery. One such valve, disclosed in U.S. Pat. No. 3,671,979 to Moulopoulos issued June 27, 1972, provides a conical, umbrella-like valve positioned on the end of an elongated catheter insertable so that the conical end of the valve is pointed upstream in the vessel. The distal end opens periodically, under the influence of reverse flow, to contact the inner walls of the vessel and prevent reverse flow while flow in the opposite direction collapses the valve around the catheter to allow flow in that direction. A problem presented by this type of valve is that the collapsed configuration provides areas of downstream stagnation which drastically increases the incidence of thrombus formation leading to reduction of the valving action and massive embolic complications.

Another type of catheter-mounted valve which, incidentally, is disclosed in FIGS. 3-5 of the above patent, but is not further described or claimed therein, utilizes an inflatable balloon on the end of the catheter which is periodically inflated by an external control to engage the walls of the vessel and block flow. Problems with this type of system are ineffective blockage of reverse flow and the requirement for an elaborate external control system to keep operation of the valve synchronous with the heart action.

SUMMARY OF THE INVENTION

This invention provides a remotely placeable artificial valve which avoids the disadvantages of the prior art by furnishing a valve system requiring no external actuation devices and formed to provide central flow of blood to minimize thrombus formation.

In a preferred embodiment the invention comprises a blood vessel valve including an expansible valve support with means biasing the support toward an open configuration where the support sealingly engages the walls of a blood vessel in which the valve is to function, a check valve mounted on the support to block flow through the vessel in one direction, a catheter associated with the support to provide for remote location of the valve and a remotely removable restraint for constraining the support to a diameter less than the inside diameter of the blood vessel to provide for movement of the valve therethrough prior to placement or removal thereof.

These and other objects and many of the attendant advantages of the invention will become better understood to those skilled in the art by reference to the following detailed description when viewed in light of the drawings wherein:

BRIEF DESCRIPTION OF THE DRAWINGS

FIG. 1 is a fragmentary perspective view of a device in accordance with the invention.

FIG. 2A is a schematic view showing the device of FIG. 1 during a phase of its installation.

FIG. 2B is a view similar to FIG. 2A showing the device of FIG. 1 in a later phase of its installation.

DETAILED DESCRIPTION OF THE DRAWINGS

Figure 3A:
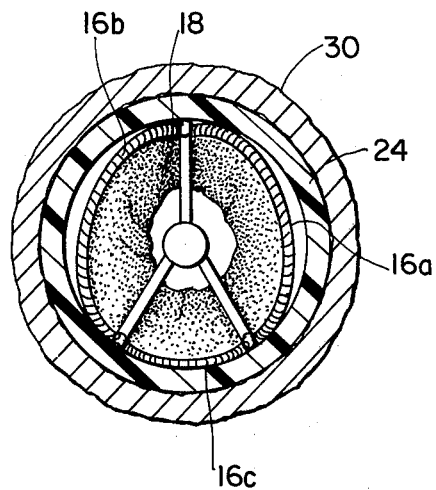
FIG. 3A is a sectional view of the device as in FIG. 2A taken along the lines 3A—3A thereof.
Figure 3B:
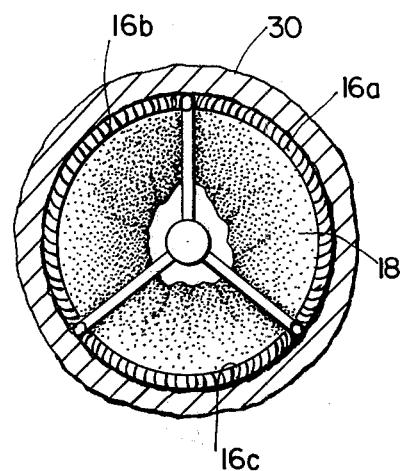
FIG. 3B is a sectional view of the device as in FIG. 2B taken along the lines 3B—3B thereof.

Referring to FIG. 1, the device shown generally at 10 includes a valve shown generally at 11 comprises a frame support 12 made up of three arms 14a, 14b, and 14c joined centrally to one another at one end and connected by three arcuate springs 16a, 16b and 16c at their other ends. The aforedescribed structure is preferably formed of an inert, corrosion-resistant material suitable for the purpose of the invention such, for example, as stainless steel spring wire or the like. The arms in size are preferably about 0.030 inch diameter wire. Springs for a ½ to 1 inch diameter valve can be composed, for example, of a 0.013 inch diameter wire wound into a 0.46 inch outer diameter coil. A suitable strength for the springs is one pound of force for one inch extension of the spring. The structure forms a valve support which, in the configuration shown in FIG. 1, is larger in effective diameter of the blood vessel in which the device is to function such that the cusps formed by the springs 16a through 16c continuously engage and form a sealing contact with the inner walls of the vessel. The structure may, however, be constrained to a smaller diameter for purposes to be described in detail below by inward radial pressure on the arms 14a through 14c to compress the springs. A tubular elastomeric membrane 18 is attached to the support 12 to surround the distal ends of the arms 14a through 14c and enclose the springs 16a through 16c as shown. The membrane is formed to provide slack between the arms 14a through 14c for purposes to be described below. The membrane may be comprised of any inert thin elastomeric material compatible with the environment of use. A biocompatible polymer such as segmented polyurethane or silicone rubber on the order of 0.003 to 0.007 inches in thickness has been found suitable for the membrane 18. Such material can also be used to coat any exposed metallic surfaces of the device to preclude thrombus formation.

An extension stem 20 is attached to the support 12 at the junction of the arms 14a through 14c. The extension stem is preferably formed of the same material as the arms 14a through 14c and is of sufficient length to reach from the point of insertion in the blood vessel to the point of installation as will be discussed below.

A constraint device generally shown at 22 comprises an open ended capsule 24 connected to a tube 26 through a smooth, tapered transition section 28. The capsule 24 is of sufficiently small outside diameter to be readily movable through a blood vessel in which the valve device 10 is to be used and is internally configured to receive the valve device fully therein through the open end when the device is collapsed by compression of the springs 16a through 16c. The tube 26 is preferably formed of an elastomer covered wire coil having sufficient length to accommodate the extension stem 20 therein. The coiled wire in the tube provides the requisite flexibility for negotiating curves within a blood vessel without putting undue stress on the walls of the vessel, serves as a guide for the extension stem 20 for purposes to be described below while, at the same time, preventing kinking of the extension stem by lending physical support therefor. The capsule 24 is preferably formed of a suitable elastomeric material such, for example, as a cloth reinforced material of sufficient strength to constrain the valve 11 therein. Ideally, for example, a suitable capsule 24 has the normal dimensions of 1 inches in length, three-eighths inch in diameter, and 0.030 inch wall thickness.

In FIGS. 2A and 3A, the device 10 is shown schematically being inserted through the femoral artery 30 toward the aortic valve 32 of the heart 34. As is adequately described in the aforedescribed prior art, insertion of this type of device is made by opening a branch of the aorta at some distance from the heart, preferably near the external surface of the body, inserting the device 10 and by applying pressure on both the extension stem 20 and tube 26, pushing the device toward the heart 34. When the device is correctly positioned, as may be verified by fluoroscopy for example, the valve 11 deployed by thrusting the extension stem 20 inward while holding the tube 26 stationary to push the valve out of the capsule 24 where the springs 16a through 16c force the frame support tightly against the vessel walls. As shown in FIG. 2B, the capsule 22 is then withdrawn by pulling tension on tube 26 and removed from the artery 30. The exterior end of the extension stem 20 is then stabilized against the surface of the body by tape or the like. If removal or readjustment of the position of the valve is required, the constraint device 22 can be reinserted and the valve 11 can be recollapsed by holding tension on the extension stem 20 and applying pressure on the tube 26 to reinsert the valve 11 into the capsule 24, followed by repositioning or removal of the device 10 as desired.

Figure 4A:
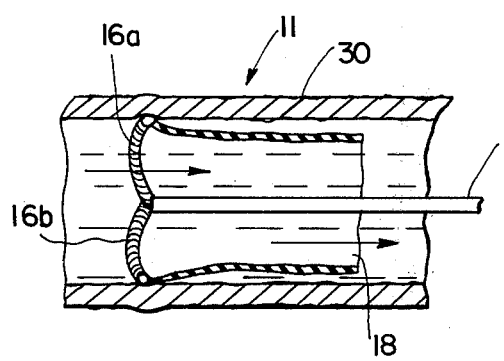
FIG. 4A is a sectional view of the device of FIG. 1 installed and during one phase of its operation coincident with systolic period of the heart.
Figure 4B:
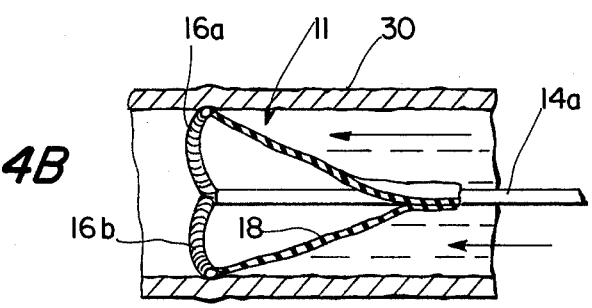
FIG. 4B is a view similar to FIG. 4A showing the device during another phase of its operation coincident with diastolic period of the heart.

As seen in FIG. 4A, the valve 11 is shown in position in the aorta 30 with forward flow of blood out of the heart as is indicated by the arrow. The membrane 18 is pushed by the flow outwardly in proximity to the walls of the vessel, thereby providing relatively unobstructed central flow of the blood relatively free of areas of possible stagnation. When flow is reversed, as is shown by the arrow in FIG. 4B, the membrane 18 is collapsed by the flow with the walls thereof, through the aforementioned slack provided, sealingly engaging to shut off reverse flow to the heart almost instantly.

The invention thereby provides a remotely insertable, repositionable, and removable prosthetic blood vessel valve which effectively checks flow in one direction while providing free, non-stagnating, central flow in the other direction without the need for external actuating devices, controls, or other support apparatus.

What has been described is illustrative of a teaching in accordance with the invention to enable those skilled in the art to practice the invention.

We claim:

1. A prosthetic valve device for remote placement in a major blood vessel to take over the function of a malfunctioning natural valve comprising:
   an expansible valve support;
   means biasing said support toward an open configuration to sealingly engage the interior walls of the blood vessel in which it is to be placed;
   check valve means in said support to block flow through said support in one direction;
   means to constrict said support in a closed configuration such that said device may be navigated through a blood vessel to a desired point of placement;
   means to remotely position said device through a blood vessel to a desired point of placement; and
   means to remotely remove said means to constrict from said support at a desired point of placement.

2. The device in accordance with claim 1 wherein said means to constrict comprises an open-ended envelope enclosing said support to maintain it in said closed configuration.

3. The device in accordance with claim 2 wherein said means to remotely position said device comprises a flexible elongated member attached to said support.

4. The device in accordance with claim 3 wherein said means to remotely remove said means to constrict comprises a flexible elongated tubular member coaxially disposed around said flexibly elongated member substantially co-extensive therewith attached to said envelope.

5. The device in accordance with claim 4 wherein said tubular membrane is helically reinforced to provide lateral support for said flexibly elongated member.

6. The device in accordance with claim 1 wherein said support comprises plural arms connected together at one end thereof and resilient spring means interconnecting the other ends of said arms to bias them apart and form a substantially conical shape.

7. The device in accordance with claim 6 wherein said spring means comprise helical compression springs bowed to form an arcuate cusp between said other ends of each of said arms in said open configuration.

8. The device in accordance with claim 7 wherein said check valve means comprises a flexible tubular membrane attached to and coaxially disposed around said frame, said membrane extending from and enclosing said compression springs to point intermediate the ends of said arms to present a substantially tubular configuration for flow therethrough toward the apex of said arms and to collapse and block flow therethrough in the opposite direction.

* * * * *

UNITED STATES PATENT OFFICE
CERTIFICATE OF CORRECTION

Patent No. 4,056,854      Dated November 8, 1977

Inventor(s) John W. Boretos and Robert A. Poirier

It is certified that error appears in the above-identified patent and that said Letters Patent are hereby corrected as shown below:

Column 3, line 18, "1 inches" should be --1 5/8 inches--.

Column 4, Claim 5, line 2, "membrane" should be --member--.

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*